United States Patent [19]

Uragami

[11] Patent Number: 4,983,303
[45] Date of Patent: Jan. 8, 1991

[54] METHOD OF SEPARATING A PARTICULAR COMPONENT FROM ITS LIQUID SOLUTION

[75] Inventor: Tadashi Uragami, Mino, Japan
[73] Assignee: Lignyte Co., Ltd., Osaka, Japan
[21] Appl. No.: 130,504
[22] Filed: Dec. 9, 1987

[30] Foreign Application Priority Data

Dec. 25, 1986 [JP] Japan .............................. 61-309991

[51] Int. Cl.⁵ .............................................. B01D 61/36
[52] U.S. Cl. ..................................... 210/640; 203/19; 203/91
[58] Field of Search ............................ 210/640, 406; 159/DIG. 27, DIG. 28, DIG. 16, 47.1; 203/19, 91, DIG. 13; 202/205

[56] References Cited

U.S. PATENT DOCUMENTS

| | | | |
|---|---|---|---|
| 2,788,316 | 7/1953 | Bjorksten | 159/DIG. 27 |
| 2,953,502 | 9/1960 | Binning et al. | 210/640 |
| 3,406,096 | 10/1968 | Rodgers | 159/DIG. 27 |
| 3,415,719 | 12/1968 | Telkes | 159/DIG. 27 |
| 3,455,792 | 7/1969 | Ohta | 159/DIG. 27 |
| 3,562,116 | 2/1971 | Rodgers | 159/DIG. 27 |
| 3,962,158 | 6/1976 | Mima et al. | 210/500.42 |
| 4,067,805 | 1/1978 | Chiang et al. | 210/640 |
| 4,111,810 | 9/1978 | Arai et al. | 210/500.27 |
| 4,125,708 | 11/1978 | Masri et al. | 210/688 |
| 4,659,590 | 4/1987 | Neidlinger et al. | 210/500.41 |
| 4,719,016 | 1/1988 | Storkebaum et al. | 210/640 |

FOREIGN PATENT DOCUMENTS

| | | |
|---|---|---|
| 0062494 | 10/1982 | European Pat. Off. . |
| 851048 | 10/1952 | Fed. Rep. of Germany . |
| 3600333 | 8/1986 | Fed. Rep. of Germany . |
| 1001922 | 2/1952 | France . |

Primary Examiner—Frank Spear
Attorney, Agent, or Firm—Armstrong, Nikaido, Marmelstein, Kubovcik & Murray

[57] ABSTRACT

A novel method of separating a particular component from its liquid solution by the use of a vessel divided into a solution chamber receiving the liquid solution and a vacuum chamber by a permeable membrane having selective permeability. The method is characterized to evacuate the vacuum chamber while keeping the liquid solution out of direct contact with the permeable membrane such that the permeation of the particular component through the permeable membrane can be effected in vapor-to-vapor phase environment, which is found to give a superior separation result for the liquid solution.

7 Claims, 2 Drawing Sheets

METHOD OF SEPARATING A PARTICULAR COMPONENT FROM ITS LIQUID SOLUTION

BACKGROUND OF THE INVENTION

1. Field of the Invention

The present invention relates to a method of separating a particular component from the liquid solution thereof through the use of a permeable membrane, and more particularly to such a method of separating the component in vapor-to-vapor phase permeation, which might be termed as an "evapomeation" method as coined from the words "evaporation" and "permeation" for well describing the novel liquid separation method of the present invention.

2. Description of the Prior Art

As a method of separating a particular component from its liquid solution or mixture such as an organic liquid containing two or more kinds of components there has been so far employed a distillation. But the distillation requires a great deal of energy input for heating the liquid solution. Hence, a reverse osmosis method is utilized as one of membrane separation methods for separating of the liquid solution. But in the reverse osmosis method, since it is required to pressurize the liquid solution under a high pressure in order that a particular component intended to be separated can permeate effectively through a permeable membrane from a more concentrated solution side to a less concentrated solution side, the permeable membrane will be readily densified by such pressurization to lower its permeation efficiency, whereby its separating performance will be considerably limited.

In this consequence, a study has been directed to a pervaporation (permeation evaporation) method which is also the membrane separation method but requires no pressurization, as shown for example in the U.S. Pat. No. 4,218,312. The principle of this pervaporation method will be briefly discussed with reference to FIG. 3 in which an apparatus for the method is schematically shown to have a separation vessel 25 divided into an upper solution chamber 23 and a lower vacuum chamber 21 by means of a permeable membrane 24. By reducing a pressure in the vacuum chamber 21 while keeping the solutions 22 introduced into the solution chamber 23 in contact with the membrane 24, a particular component in the liquid solution 22 will permeate and diffuse through the permeable membrane 24 selectively in preference to the other components so that the component having permeated can evaporate from the surface of the permeable membrane 24 into the vacuum chamber 21. With this method, it is possible to effect the separation of the liquid solution by recovering the particular component thus permeated through the membrane 24 and evaporated into the vacuum chamber 21 or alternatively by recovering the remaining solution in the solution chamber 23.

As explained in the above, the pervaporation method enables to separate the liquid solution through a permeable membrane without requiring any pressurization as in the reverse osmosis method and also without causing the membrane to be undesirably densified.

However, in the above pervaporation method in which the liquid solution is kept in direct contact with the permeable membrane, there arises another problem that the permeable membrane which is generally made from a macromolecular material is likely to be swelled due to the direct contact with the solution. When the permeable membrane is swelled, its permeability will be degraded to thereby lower the separation efficiency.

SUMMARY OF THE INVENTION

In view of the above drawbacks, the present invention has been accomplished. Accordingly the primary object of the present invention is to provide a method of separating a particular component at an improved efficiency from its liquid solution by the use of a permeable membrane without causing the membrane to be swelled with the solution.

An improved method of separating a particular component from its liquid solution in accordance with the present invention utilizes a separation vessel which is divided into a solution chamber and a vacuum chamber by means of a permeable membrane. The method comprises the steps of introducing into the solution chamber a liquid solution containing the component to be separated and maintaining the liquid solution out of direct contact with the permeable membrane, and evacuating the vacuum chamber in order to evaporate the solution and selectively permeate the resulting vapor through the permeable membrane from the solution chamber into the vacuum chamber.

With the separation method of the present invention, the permeable membrane can be kept free from being swelled with the liquid solution so that the permeation can continue during the entire course of separation at its maximum efficiency, thereby greatly enhancing the overall separation efficiency.

DETAILED DESCRIPTION OF THE INVENTION

Figure 1:
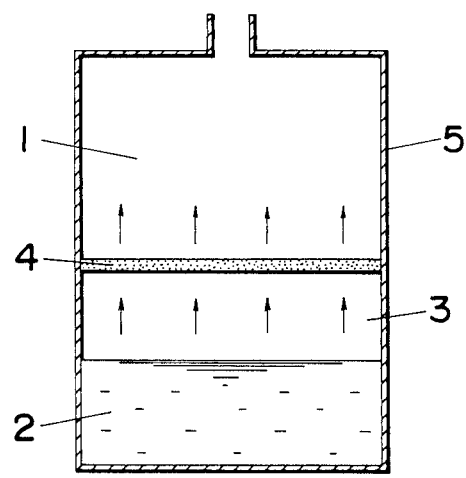
FIG. 1 is a schematic view showing an apparatus used for the present invention.

Referring to FIG. 1 which illustrates the principle of the "evapomeation" separation method of the present invention, a separation vessel 5 is divided by means of a permeable membrane 4 into an upper vacuum chamber 1 and a lower solution chamber 3. The permeable membrane 4 is selected depending upon a particular component of the liquid solution intended to be separated. A clearance or space is provided between the undersurface of the membrane 4 and the surface of the liquid solution 2 stored in the solution chamber 3 so as to keep the permeable membrane 4 out of direct contact with the liquid solution 2. As evacuating the vacuum chamber 1, the solution chamber 3, which is in air communication therewith through the permeable membrane 4, is correspondingly evacuated to cause the liquid solution to evaporate. When the vapor from the liquid solution thus evaporated comes into contact with the permeation membrane 4, it permeates through the membrane 4 as it diffuses therein and is forced to enter the vacuum chamber 3 under the effect of the vacuum. Since the permeable membrane 4 allow a particular component to selectively permeate in preference to the others, it is readily possible to complete the separation either by collecting the component having passed into the vacuum chamber 1 through the permeable membrane 4 or by collecting the remaining solution in the solution chamber 3 from which the component has been removed.

As seen in the above, the separation of the liquid solution 2 can be carried out in the form of the vapor-to-vapor phase permeation through the membrane 4. Consequently, the membrane 4 can be kept free from substantial swelling which is inherent where the membrane is in direct contact with the liquid solution as in the conventional pervaporation method, effectively preventing the permeable membrane from lowering its permeation efficiency. This, in addition to the fact that the permeation is carried out in vapor-to-vapor phase, results in a remarkably high permeation rate of the selective component as compared to the conventional pervaporation method in which the separation is made in the liquid-to-vapor phase permeation. Therefore, the method according to the present invention, which might be called the "evapomeation" method, makes it possible to enhance the permeating and separating efficiency for the liquid solution.

The permeable membrane 4 utilized in the present invention may be a membrane which is generally called a non-porous membrane including those utilized in the conventional pervaporation method. For example, the permeable membrane may be made from alginic acid, chitosan, cross-linked chitosan, chitosan acetate, quaternized chitosan, polystyrene, polyvinylidenechloride, silicon (polydimethylsiloxane), polyvinylidenefluoride, cellulose nitrate, cellulose acetate, polyvinylalcohol, and the like material.

Even the permeable membrane made from the material which is easily swelled by the contact with the liquid solution can be equally utilized in the present invention without lowering the separation efficiency. Since the present invention places no substantial limitation on the kinds of material forming the permeable membrane, the separation can be made at a most effective manner by selecting from a wide variety of materials a most optimum one as the permeable membrane depending upon the particular component to be separated.

In view of the fact that the permeation rate of the particular component is inversely proportional to the thickness of the membrane through which it permeates and that the permeation effect has no direct relation to the membrane thickness, the permeation rate can be increased by employing a thinner membrane.

Further, in view of that the permeation rate will vary depending upon the degree of the negative pressure developed behind the membrane, it can be also increased by raising the degree of vacuum in the vacuum chamber.

When the permeable membrane of a reduced thickness is utilized, it is preferred to place the membrane on a support member for reinforce the membrane enough to resist against a negative pressure developed therebehind. The support member may be in the form of a net or a porous plate, for example, a porous glass plate provided between the vacuum chamber and the solution chamber for preventing the breakage of the membrane under the effect of the negative pressure.

Figure 2:
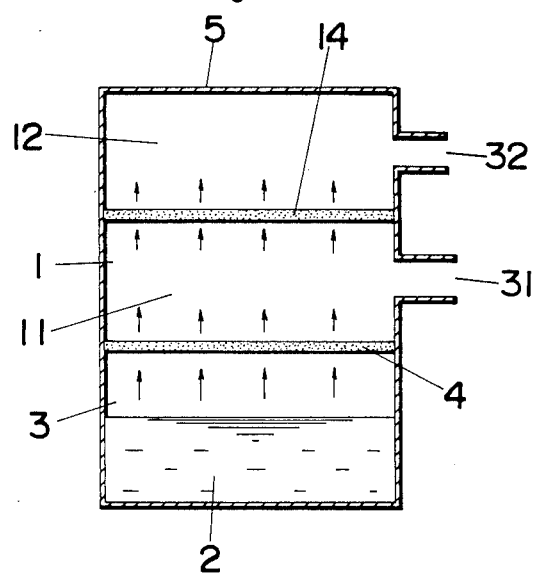
FIG. 2 is a schematic view showing another apparatus used for the present invention.

FIG. 2 illustrates another apparatus utilized for the liquid separation which is advantageous in carrying out the present invention. In this apparatus, an additional permeable membrane 14 is utilized to subdivide the vacuum chamber 1 of FIG. 1 into a pair of first and second vacuum chambers 11 and 12 each provided with an evacuation port 31, 32.

When the apparatus of FIG. 2 is utilized for separation of an aqueous solution of alcohol, the permeable membrane 4 is selected to be made of an alcoholphile material allowing selective permeation of alcohol in preference to water, while the permeable membrane 14 is selected to be made of hydrophilic material allowing selective permeation of water in preference to alcohol. Upon reaching to a suitable degree of vacuum in the first and second chambers 11 and 12, the alcohol contained in the resulting vapor of the liquid solution will preferentially permeate through the lower membrane 4 to raise the alcohol concentration in the vapor proceeding into the first chamber 11. Then, the water content in the vapor within the first chamber 11 will be caused to permeate preferentially through the upper membrane 14 into the upper second chamber 12, thereby further raising the alcohol concentration of the vapor entrapped within the first chamber 11. With this result, the alcohol can be recovered at an increased concentration from the first chamber 11 through the port 31. In addition, the water separated through the permeation membranes 4 and 14 can be easily recovered from the chamber 12 through the port 32.

In the like manner, three or more components can be readily separated by adding the corresponding number of permeable membranes having different preferential selectivity.

Although the method according to the present invention can be adapted to the separation of any kinds of components from its liquid solution by suitably selecting the permeable membrane or membranes, it is found to be particularly effective for the separation of the liquid solution which is difficult to be separated by an usual distillation method. For example, the present invention can be applied effectively to the systems of separating alcohol, aromatic compound or ether from azeotropic mixtures such as water-alcohol solution, water-aromatic compound solution or water-ether solution, of separating one or more of organic solvents such as hydrocarbons having close boiling points from the mixture thereof, of separating one or more of structural isomers such as o-, m- or p-xylene from the mixture thereof, of separating one or more of dextrorotatory or levorotatory optical isomers from the mixture thereof, of separating thermal decompositional or transmutational components such as medicines, substances relating to a living body, fruit juices or polymerized monomers from the mixtures thereof, of separating a reaction product from a reacting mixture in order to shift the reaction equilibrium for promoting the reaction, or of separating one or more of volatile organic components such as ammonia, amine, hydrogen sulfide, carbon dioxide or sulfurous acid gas from waste liquids.

In addition, the present invention can be also applied to the systems of concentrating alcohol from a biomass, of recovering expensive organic solvents such as dimethylformamide, dimethylacetamide or dimethylsulfoxide from synthetic fiber spinning bath, of recovering solvents from a waste paint liquid dissipated during the process of paint manufacturing or at a painting line, of concentrating alcohol or organic solvent from the mixture thereof utilized in a chemical facility, of recovering salts from the mixture thereof, of recovering trichloroethylene from the dry cleaning mixture, of concentrating an emulsion solution or a solution containing a radioactive substance, of concentrating a rare earth ion in its solution, of concentrating a virus or bacteriophage, of manufacturing sterile water or nonexothermic water for medicine formulation, hospital use or hemodialysis, or of manufacturing ultrapure water for an electronic industry.

The present invention will be discussed with reference to the following examples, which are provided by way of illustration and not by way of limitation. All percent is by weight.

EXAMPLE 1

A 0.5% aqueous solution of sodium alginate was deaerated under a negative pressure condition to prepare a casting solution. The casting solution was then poured evenly on a flat Petri dish and was placed within a thermostat drier where it was dried at a temperature of 60° C. for 6 hours to completely evaporate the solution in order to form a sodium alginate membrane. After being peeled from the dish, the sodium alginate membrane was immersed into a 1N hydrochloric acid of 25° C. for 24 hours to obtain an alginic acid membrane. The resulting alginic acid membrane was washed repeatedly with pure water until residual hydrochloric acid was completely removed therefrom, or no chlorine ion was detected in the washing water. Thereafter, it was dried to present the alginate acid membrane of 3 μ in dry thickness which is a permeable membrane having selective permeability to water in preference to alcohol.

The alginic acid membrane thus obtained was utilized as the permeable membrane 4 dividing the separation vessel 5 of FIG. 1 into the upper vacuum chamber 1 and the lower solution chamber 3. Samples 1 to 8 which are aqueous solutions of different ethanol concentrations, were each introduced into the solution chamber 3 in order to effect the separation of the aqueous solution by evacuating the vacuum chamber 1 down to a pressure of $10^{-2}$ Torr. at a temperature of 40° C. A permeation rate and a separation factor $\alpha$ were obtained for each sample for evaluation of permeation efficiency, as listed in Table 1.

COMPARATIVE EXAMPLE 1

Figure 3:
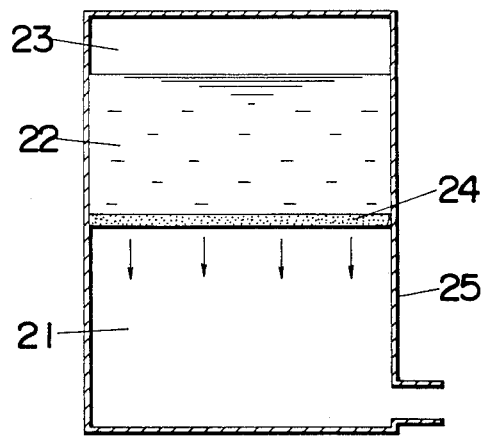
FIG. 3 is a schematic view illustrating a general pervaporation method.

The same permeable membrane of alginic acid as obtained in Example 1 was utilized as the membrane 24 of the apparatus of FIG. 3 to carry out the pervaporation method for comparison with the method of the present invention. For this purpose, like samples of different ethanol concentrations are each tested to provide the permeation rate and separation factor $\alpha$ under the same conditions as in Example 1 except that the membrane 24 was swelled to have an increased wet thickness of 20 μ due to the direct contact with the liquid solution. The test results are also listed in Table 1.

The separation factor $\alpha$ in Table-1 is defined by the following equation:

$$\alpha = \frac{Y_{H2O}/Y_{ETOH}}{X_{H2O}/X_{ETOH}}$$

wherein $X_{H2O}$ and $X_{ETOH}$ are fractions of water and ethanol respectively in aqueous ethanol solution received in the solution chamber 3, 23, while $Y_{H2O}$ and $Y_{ETOH}$ are fractions of water and ethanol respectively in the vapor after permeating through the membrane 4, 14 as measured in the subsequently liquified phase. As apparent from the above relation, when $\alpha$ is greater than 1, it means that the water has passed through the membrane 4, 24 in a greater amount than the ethanol and that the water is allowed to pass preferentially through the membrane to a larger extent as the value $\alpha$ becomes greater. It is noted in this connection that the permeation rate in Table 1 is defined as a rate at which the water and ethanol having the proportion represented by the value $\alpha$ has permeated through the membrane.

TABLE 1

| | ethanol concentration [wt %] in | Example 1 | | Comparative Example 1 | |
|---|---|---|---|---|---|
| Sample | liquid solution | permeation rate [kg/m². hr] | separation factor [α] | permeation rate [kg/m². hr] | separation factor [α] |
| 1 | 0 | 0.24 | 1.0 | 0.092 | 1.0 |
| 2 | 10 | 0.18 | 4.5 | 0.11 | 0.63 |
| 3 | 30 | 0.20 | 5.5 | 0.18 | 0.67 |
| 4 | 50 | 0.21 | 5.8 | 0.11 | 0.85 |
| 5 | 70 | 0.23 | 7.3 | 0.052 | 16.0 |
| 6 | 90 | 0.13 | 295.0 | 0.016 | 32.0 |
| 7 | 96 | $7.5 \times 10^{-3}$ | 1940.0 | 0.048 | 8.8 |
| 8 | 100 | $2.4 \times 10^{-3}$ | 1.0 | 0.11 | 1.0 |

As apparent from Table 1, Example 1 embodying the "evapomeation" method of the present invention shows greater values in both the permeation rate and the separation factor $\alpha$ in every samples of differing ethanol concentrations than Comparative Example 1 embodying the conventional "pervaporation" method. Thus, it is confirmed that the "evapomeation" method of the present invention can make the best of the function of the permeable membrane, i.e., the function of allowing the water to preferentially permeate therethrough for the purpose of increasing the concentration of the ethanol in its solution and therefore making the liquid separation most effectively. It should be particularly noted that, as shown from the results of sample no. 7, a highest separation factor $\alpha$ indicative of good separation results can be obtained even for an azeotropic mixture having an ethanol concentration of as high as 96% which is hardly possible to be separated with the conventional distillation method. This means that the "evapomeation" method of the present invention enables the permeable membrane to allow the preferential permeation of water at a remarkably high rate enough to remove the water from such azeotropic mixture, and consequently finds itself to be most suitable for purification of azeotropic mixture.

EXAMPLE 2

A 1% solution of chitosan in a 1N aqueous solution of acetic acid was deaerated under a negative pressure condition to prepare a casting solution, which was subsequently poured evenly on a flat Petri dish and placed within a thermostat drier where it was dried at a temperature of 60° C. for 6 hours to completely evaporate in order to form a chitosan acetate membrane. After being peeled from the dish, the chitosan acetate membrane was immersed into an aqueous solution of 1N sodium hydroxide to obtain a chitosan membrane. The resulting chitosan membrane was washed repeatedly with pure water until residual sodium hydroxide was completely removed therefrom, or no sodium ion was detected in the washing water. Thereafter, it was dried to present the chitosan membrane of 5 μ in dry thickness which is a permeable membrane having selective permeability to water in preference to ethanol.

The chitosan membrane thus obtained was utilized as the membrane 4 in the vessel 5 of FIG. 1 so as to conduct the tests in the same procedures as in Example 1 for each of the samples 1 to 8 of different ethanol concentrations. The test results of the permeation rate and the separation factor α are listed in Table 2.

COMPARATIVE EXAMPLE 2

The same chitosan membrane as obtained in Example 2 was utilized as the membrane 24 of the apparatus of FIG. 3 to carry out the conventional pervaporation method for a comparison purpose. In this comparative example, like samples 1 to 8 were each tested for obtaining the permeation rate and the separation factor α under the same condition as in Example 2 except that the membrane was swelled to have an increased wet thickness of 30 μ due to the direct contact with the liquid solution. The test results were also listed in Table 2.

TABLE 2

| | | Example 2 | | Comparative Example 2 | |
|---|---|---|---|---|---|
| Sample | ethanol concentration [wt %] in liquid solution | permeation rate [kg/m² · hr] | separation factor [α] | permeation rate [kg/m² · hr] | separation factor [α] |
| 1 | 0 | 0.35 | 1.0 | 0.14 | 1.0 |
| 2 | 10 | 0.31 | 4.7 | 0.19 | 1.41 |
| 3 | 30 | 0.25 | 5.8 | 0.14 | 2.08 |
| 4 | 50 | 0.17 | 7.5 | 0.067 | 7.3 |
| 5 | 70 | 0.091 | 33.0 | 0.035 | 27.0 |
| 6 | 90 | 0.018 | 115.0 | 0.012 | 52.0 |
| 7 | 96 | 0.007 | 202.0 | 0.003 | 78.0 |
| 8 | 100 | 0.072 | 1.0 | 0.006 | 1.0 |

As seen from Table 2, Example 2 embodying the "evapomeation" method of the present invention shows greater values in both the permeation rate and the separation factor α with respect to every samples 1 to 8 of differing ethanol concentrations than Comparative Example 2 embodying the conventional "pervaporation" method. Also, it is confirmed that Example 2 is successful to provide a highest separation factor α with respect to sample no. 7, which is an azeotropic mixture having an ethanol concentration of as high as 96%, and thus assures good separation effect for such azeotropic mixture.

EXAMPLE 3

A 3.5% solution of polystyrene in benzene was poured onto a flat Petri dish and stood for 3 hours in a temperature of 25° C. to obtain a polystyrene permeable membrane of 15 μ in dry thickness. The polystyrene membrane thus obtained was utilized as the permeable membrane 4 of the vessel of FIG. 1 for conducting the same tests as in Example 1 for each of the samples 1 to 8 under the same conditions. The test results of the permeation rate and the separation factor α are listed in Table 3.

TABLE 3

| sample | ethanol concentration [wt %] in liquid solution | permeation rate [×10⁻³ kg/m² · hr] | separation factor [α] |
|---|---|---|---|
| 1 | 0 | 4.5 | 1 |
| 2 | 10 | 9.2 | 30 |
| 3 | 30 | 5.7 | 33 |
| 4 | 50 | 4.1 | 37 |
| 5 | 70 | 4.0 | 42 |
| 6 | 90 | 3.3 | 146 |
| 7 | 96 | 4.1 | 356 |

TABLE 3-continued

| sample | ethanol concentration [wt %] in liquid solution | permeation rate [×10⁻³ kg/m² · hr] | separation factor [α] |
|---|---|---|---|
| 8 | 100 | 3.1 | 1 |

It is seen from Table 3 that the use of the polystyrene permeable membrane in the "evapomeation" method of the present invention causes no substantial difference in the permeation rate between the samples 1 to 8 of different ethanol concentrations. Further, it is confirmed that the polystyrene membrane has the separation factor α of greater than 1 for each sample to allow the water to preferentially permeate therethrough and that it has a greatest separation factor α for the azeotropic mixture of sample no. 7 having an ethanol concentration of 96%.

EXAMPLE 4

In this example, the apparatus of FIG. 2 was utilized for separating water and ethanol from the mixture solution thereof in accordance with the "evapomeation" method of the present invention. A polydimethylsiloxane membrane was utilized as the permeable membrane 4 allowing the ethanol to selectively permeate in preference to the water, while a membrane of chitosan cross-linked with dialdehyde was utilized as the permeable membrane 14 allowing the water to selectively permeate in preference to the ethanol. The dialdehyde cross-linked chitosan membrane was prepared by immersing the chitosan membrane obtained in Example 2 for 15 minutes into a 0.4% aqueous solution of glutaraldehyde, to which was added an 0.5N aqueous solution of sulfuric acid as a catalyst, so as to cross-link the chitosan with aldehyde followed by washing it and then drying it under a negative pressure at a room temperature.

Samples 9 to 14, which are aqueous solution of different ethanol concentrations, were each introduced into the solution chamber 3 and was then subjected to a test for separating ethanol from the liquid solution. The test was conducted for an hour in an ambient temperature of 40° C. by evacuating the upper vacuum chamber 12 through the upper port 32 to a reduced pressure level of $10^{-2}$ Torr for a hour with the port 31 of the lower vacuum chamber 11 closed. The ethanol concentrations of the vapor in the solution chamber 3, of the vapor in the lower vacuum chamber 11 were measured respectively for each sample after completing the above test. The test results are listed in Table 4 together with comparison results which were obtained by comparison tests which were made under the same conditions in the above except that the membrane 14 was removed from the vessel 5 to utilize only the polydimethylsiloxane membrane 4 showing the selective permeability to ethanol, with respect to the same samples 9 to 14.

TABLE 4

| | | Example 4 | | Comparison ethanol |
|---|---|---|---|---|
| sample | ethanol concentration [wt %] in liquid solution | ethanol concentration [wt %] in vapor of chamber 3 | ethanol concentration [wt %] in vapor of chamber 11 | concentration [wt %] in vapor of chamber 11 without membrane 14 |
| 9 | 10 | 43.9 | 76.8 | 61.5 |
| 10 | 30 | 60.4 | 82.3 | 75.5 |
| 11 | 50 | 67.7 | 86.0 | 82.3 |
| 12 | 70 | 77.3 | 90.0 | 86.1 |

TABLE 4-continued

| | Example 4 | | Comparison ethanol |
|---|---|---|---|
| sample | ethanol concentration [wt %] in liquid solution | ethanol concentration [wt %] in vapor of chamber 3 | ethanol concentration [wt %] in vapor of chamber 11 | concentration [wt %] in vapor of chamber 11 without membrane 14 |
| 13 | 90 | 90.8 | 94.1 | 93.1 |
| 14 | 95.6 | 95.6 | 98.0 | 97.1 |

As seen from Table 4, it is proved that ethanol can be recovered at a higher concentration with the combination use of the permeable membranes one having selective permeability to ethanol and the other to water, than the single use of the permeable membrane having selective permeability to ethanol. It is noted at this time that with the use of the vessel of FIG. 2 the ethanol of high concentration can be easily recovered through the lower port 31.

What is claimed is:

1. A method for separating a liquid component from a solution containing two or more liquid components, which comprises:
    (a) providing a vessel divided by a permeable membrane into a solution chamber and a vacuum chamber, said membrane being selectively permeable to the vapors of the component to be separated;
    (b) placing the solution into the solution chamber out of direct contact with the permeable membrane;
    (c) applying a vacuum to the vacuum chamber to evaporate the solution in the solution chamber and draw the resulting vapors through the permeable membrane into the vacuum chamber, whereby the component to be separated selectively permeates through the membrane in a vapor-to-vapor phase environment.

2. The method as set forth in claim 1, wherein the solution is an aqueous solution of ethanol.

3. The method as set forth in claim 2, wherein the permeable membrane is an alginic acid membrane selectively permeable to water.

4. The method as set forth in claim 2, wherein the permeable membrane is a chitosan membrane selectively permeable to water.

5. The method as set forth in claim 2, wherein the permeable membrane is a polystyrene membrane selectively permeable to water.

6. A method for separating liquid components from a solution containing two liquid components which comprises:
    (a) providing a vessel divided by a permeable membrane into a solution chamber and a vacuum chamber, said membrane being selectively permeable to the vapors of one of the components to be separated, said vacuum chamber being subdivided into a first vacuum chamber and a second vacuum chamber by a second permeable membrane, said second permeable membrane being selectively permeable to the vapors of the other component to be separated;
    (b) placing the solution into the solution chamber out of direct contact with the first permeable membrane;
    (c) applying a vacuum to the second vacuum chamber to evaporate the solution in the solution chamber and draw the resulting vapors through the first and second permeable membranes, whereby the first component to be separated selectively permeates through the first permeable membrane in a vapor-to-vapor phase environment into the first vacuum chamber and the second component to be separated selectively permeates through the second membrane in a vapor-to-vapor phase environment into the second vacuum chamber.

7. The method as set froth in claim 6, wherein the solution is an aqueous solution of ethanol, the first permeable membrane is a polydimethylsiloxane membrane selectively permeable to the ethanol, and the second permeable membrane is a dialdehyde cross-linked chitosan membrane selectively permeable to water.

* * * * *